US008911957B2

(12) United States Patent (10) Patent No.: US 8,911,957 B2
Irimia et al. (45) Date of Patent: Dec. 16, 2014

(54) DEVICES AND METHODS FOR DETECTING CELLS AND OTHER ANALYTES

(75) Inventors: Daniel Irimia, Charlestown, MA (US); Xuanhong Cheng, Charlestown, MA (US); Mehmet Toner, Wellesley, MA (US); Utkan Demirci, Cambridge, MA (US); William Rodriguez, Arlington, MA (US)

(73) Assignee: The General Hospital Corporation, Boston, MA (US)

( * ) Notice: Subject to any disclaimer, the term of this patent is extended or adjusted under 35 U.S.C. 154(b) by 1084 days.

(21) Appl. No.: 12/293,046

(22) PCT Filed: Mar. 15, 2007

(86) PCT No.: PCT/US2007/006791
§ 371 (c)(1),
(2), (4) Date: May 21, 2009

(87) PCT Pub. No.: WO2007/106598
PCT Pub. Date: Sep. 20, 2007

(65) Prior Publication Data
US 2009/0298067 A1 Dec. 3, 2009

Related U.S. Application Data

(60) Provisional application No. 60/782,470, filed on Mar. 15, 2006.

(51) Int. Cl.
*G01N 33/543* (2006.01)
*G01N 33/53* (2006.01)
*G01N 33/569* (2006.01)

(52) U.S. Cl.
CPC .... *G01N 33/56972* (2013.01); *G01N 33/56966* (2013.01); *Y10S 436/824* (2013.01)
USPC ............. 435/7.2; 435/7.1; 436/501; 436/518; 436/824

(58) Field of Classification Search
USPC ..................... 435/7.1, 7.2; 436/501, 518, 824
See application file for complete search history.

(56) References Cited

U.S. PATENT DOCUMENTS 5,215,926 A * 6/1993 Etchells et al. ............... 436/501
6,251,615 B1 * 6/2001 Oberhardt .................... 435/7.21
(Continued)

FOREIGN PATENT DOCUMENTS

WO WO2004/029221 4/2004

OTHER PUBLICATIONS

Israeli Office Action dated Dec. 2, 2010 issued in corresponding Israeli patent application No. 194101 in Hebrew with English translation.

(Continued)

*Primary Examiner* — Melanie Y Brown
(74) *Attorney, Agent, or Firm* — Fish & Richardson P.C.

(57) ABSTRACT

The invention features methods, devices, and kits for the isolation of analytes (e.g., a cell). A sample containing a desired analyte is introduced into a microfluidic device containing moieties that bind the desired analyte. A shear stress is applied that is great enough to prevent binding of undesired analytes and low enough to allow binding of the analyte of interest. Once bound, the desired analytes can be analyzed (e.g., counted). The invention also features methods for determining a shear stress for isolating a desired analyte.

11 Claims, 10 Drawing Sheets

(56) References Cited

U.S. PATENT DOCUMENTS

| | | | | |
|---|---|---|---|---|
| 2002/0006664 | A1* | 1/2002 | Sabatini | 435/456 |
| 2003/0190368 | A1* | 10/2003 | Stoughton et al. | 424/556 |
| 2003/0219713 | A1 | 11/2003 | Valencia et al. | |
| 2004/0067544 | A1* | 4/2004 | Vogel et al. | 435/7.32 |
| 2004/0132642 | A1* | 7/2004 | Hwang | 514/9 |
| 2006/0073095 | A1* | 4/2006 | Kessler | 424/1.11 |
| 2006/0223195 | A1 | 10/2006 | Meyer et al. | |
| 2008/0194508 | A1* | 8/2008 | Christensen et al. | 514/44 |
| 2009/0253204 | A1* | 10/2009 | King et al. | 435/395 |

OTHER PUBLICATIONS

Chinese Office Action dated Sep. 23, 2011 issued in corresponding Chinese patent application No. 200780017396.9 with English-language translation.

Examination Report from corresponding CN application 200780017396.9 dated Mar. 1, 2013 and corresponding English language translation.

Sin Aaron et al.: "Enrichment Using Antibody-coated Microfluidic Chambers in Shear Flow: model mixtures of human lymphocytes." Biotechnology and Bioengineering, Sep. 30, 2005, vol. 91, No. 7, pp. 816-826, XP002567592, ISSN: 0006-3592.

Murthy Shashi K. et al.: "Effect of Flow and Surface Conditions on Human Lymphocyte Isolation Using Microfluidic Chambers." Langmuir: The ACS Journal of Surfaces and Colloids, Dec. 21, 2004, vol. 20, No. 26, pp. 11649-11655, XP002567593 ISSN: 0743-7463.

Chang Wesley C. et al.: "Biomimetic Technique for Adhesion-based Collection and Separation of Cells in a Microfluidic Channel." Lab on a Chip, Jan. 2005, vol. 5, No. 1, pp. 64-73, XP002567594 ISSN 1473-0197.

Chang W. C. et al.: A Biomimetic Method for Extracting Leukocytes from Blood in Microfluidic Devices, 2nd Annual International IEEE-EMBS Special Topic Conference on Microtechnologies in Medicine and Biology. Proceedings (CAT. No. 02EX578) IEEE Piscataway, NJ, U.S.A., 2002, pp. 184-188, XP002567596 ISBN: 0-7803-7480-0.

Chang W. C. et al.: "Adhesion-based Capture and Separation of Cells for Microfluidic Devices," Materials Research Society Symposium—Proceedings 2002 Materials Research Society U.S., vol. 729, 2002, pp. 155-160, XP002567595.

Kashanim D. et al.: "Microfluidic Biochips for Cell Guidance and Separation," 1st Annual International IEEE-EMBS Special Topic Conference on Microtechnologies in Medicine and Biology. Proceedings (CAT. No. 00EX451) IEEE Piscataway, NJ, U.S.A., 2000, pp. 279-282, XP002567597 ISBN: 0/7803-6603-4.

Radisic Milica et al.: "Micro- and Nanotechnology in Cell Separation." International Journal of Nanomedicine 2006, vol. 1, No. 1, pp. 3-14, XP002567598 ISSN: 1176-9114.

European Search Report for App. Ser. No. EP 07 75 3420, dated Feb. 10, 2010, 12 pages.

Written Opinion from Australian Patent Office for App. Ser. No. SG-200806804-1, dated Aug. 26, 2009, 5 pages.

\* cited by examiner

US 8,911,957 B2

DEVICES AND METHODS FOR DETECTING CELLS AND OTHER ANALYTES

CROSS-REFERENCE TO RELATED APPLICATIONS

This application is a National Stage application under 35 U.S.C. §371 and claims benefit under 35 U.S.C. §119(a) of International Application No. PCT/US2007/006791, filed on Mar. 15, 2007, which, in turn, claims benefit of U.S. Provisional Application No. 60/782,470, filed Mar. 15, 2006, which is hereby incorporated by reference in its entirety.

BACKGROUND OF THE INVENTION

This invention relates to the fields of medical devices, medical diagnostics, and cell counting.

Of the 40.4 million people infected with HIV globally, more than 35 million live in developing countries with significant resource limitations, many of whom are in urgent need of diagnosis, monitoring and antiretroviral therapy. In the process of managing HIV-infected subjects, counts of a specific white blood cell population, CD4+ T lymphocytes, have proven to be essential biological indicators. In adults, the absolute number of CD4+ T cells per microliter of blood has critical prognostic and therapeutic implications and is used for both HIV staging and treatment decisions. Regular monitoring of CD4 counts—two to four times per year—is recommended for all stages of infection. Clinically, a CD4 count below 200 cells $mL^{-1}$ establishes the diagnosis of AIDS and in most settings is used as a marker to initiate antiretroviral treatment (ART) and prophylaxis against opportunistic infections. Higher CD4 count thresholds of 350 and 500 cells $mL^{-1}$ are widely used as markers to increase the intensity of monitoring, and in some settings, to initiate ART. However, affordable and appropriate laboratory monitoring tools to determine CD4 counts have little penetration in resource-limited settings, despite ongoing international efforts to extend the availability of ART to these areas.

Currently, the gold standard for CD4+ T cell enumeration is flow cytometric counting of lymphocyte subpopulations using monoclonal antibodies and commercial multi-purpose flow cytometers or single-purpose CD4-counting flow cytometers. Although these instruments are high throughput and accurate, their cost and technical requirements for operation and maintenance have limited their reach and significantly delayed the implementation of HIV treatment programs in resource-limited areas worldwide. Smaller instruments like the Guava EasyCD4 offer limited improvements and have not been widely adopted. Non-cytofluorographic methods, including ELISA and bead format assays have been suggested as useful alternatives for CD4+ T lymphocyte quantification, since these methods require less equipment and have lower reagent costs than flow cytometry. However, they have much lower throughput, are more labor intensive and less accurate, and are not widely used or recommended by World Health Organization guidelines.

In addition, improvements on the back-end aspects of CD4 counting—such as miniaturization of equipment—do not address the most problematic issue for resource-limited settings, which is sample preparation. The requirements to collect blood by venipuncture, to lyse erythrocytes, to centrifuge samples, or to use pipettes for any step in the diagnostic assay are extremely problematic in these settings.

Accordingly there is still a need for low cost methods for the diagnosis and monitoring of CD4 cell populations.

SUMMARY OF THE INVENTION

The invention features a method for isolating a desired cell from a sample by introducing the sample into a microfluidic device containing a binding moiety specific for the desired cell, allowing desired cells in the sample to bind to the binding moiety, and applying a shear stress to the microfluidic device so that desired cells remain bound while undesired cells do not. In this embodiment, the step of allowing the desired cells to bind to the binding moiety and the step of applying a shear stress, can occur simultaneously.

The invention also features a method for isolating a desired cell from a sample by introducing the sample into a microfluidic device containing a first binding moiety specific for a first desired cell disposed in a first chamber. This method includes allowing the first desired cell in the sample to bind to the first binding moiety, applying a first shear stress to the microfluidic device so the first desired cells remain bound while other cells do not, and allowing the remaining sample to flow into a second chamber of the microfluidic device containing a binding moiety for a second desired cell. This method further includes allowing second desired cells in the sample to bind to the second binding moiety and applying a second shear stress to the second chamber so the second desired cells remain bound while undesired cells do not. In this embodiment the first shear stress and the second shear stress can be the same or different. Also in this embodiment, the first binding moiety and the second binding moiety can be the same or different. As above, the stress may be applied at the same time as binding occurs.

The invention further features a kit for isolating a desired cell. This kit includes a device including a chamber containing a binding moiety specific for the desired cell, and a pump for producing a shear stress so that the desired cells bind preferentially compared to undesired cells. This kit can also include a labeling reagent specific for the desired cell. Optionally, this kit can also include instructions for AIDS diagnosis.

In another aspect, the invention features a method of determining a shear stress for isolating a desired cell on a device. This method includes introducing a sample containing the desired cell into a chamber of a microfluidic device, the chamber containing a binding moiety specific for the desired cell, allowing desired cells in the sample to bind to the binding moiety, and applying shear stress to the microfluidic device. In this method the shear stress is varied along the length of the chamber and a shear stress at which the desired cell binds to the binding moiety preferentially compared to another cell is identified. In this aspect, the shear stress may be applied at the same time as binding occurs In any of the forgoing aspects, the binding moieties can be selected from antibodies, antibody fragments, oligo- or polypeptides, nucleic acids, cellular receptors, ligands, aptamers, MHC-peptide monomers or oligomers, biotin, avidin, oligonucleotides, coordination complexes, synthetic polymers, and carbohydrates.

Also in any of the forgoing aspects, the sample can be a blood sample, the binding moiety can bind to CD66, CD14, CD4, CD8, EpCAM, E-Selectin, or P-Selectin, and the desired cell can be selected from neutrophils, monocytes, lymphocytes, circulating tumor cells, HIV infected CD8 lymphocytes, circulating endothelial cells, and platelets.

In a preferred embodiment, the desired cells are CD4+ lymphocytes. In this embodiment, the sample may be obtained from a patient at risk of developing AIDS.

Methods of the invention can also include analyzing at least one property (e.g., biological property) of the desired cells (e.g., mRNA expression, protein expression, DNA quantification, DNA sequence, and chromosomal abnormalities); counting the desired cells (e.g., CD4+ lymphocytes), e.g., to diagnose a disease state such as AIDS.

Although described in terms of cells, the methods, devices, and kits of the invention may be employed in conjugation with other analytes, as described herein.

In preferred embodiments, desired cells bind preferentially compared to other cells capable of binding to the binding moiety in the absence of shear stress.

By a "patient" is meant a living multicellular organism. The term "patient" is meant to include humans, mice, dogs, cats, cows, sheep, horses, non-human primates, and fish.

By "binding moieties" is meant a molecule that specifically binds to an analyte (e.g., a cell). Binding moieties include, for example, antibodies, aptamers, receptors, ligands, antigens, biotin/avidin, metal ions, chelating agents, nucleic acids, MHC-peptide monomers, tetramers, pentamers or other oligomers.

By "cell surface marker" is meant a molecule bound to a cell that is exposed to the extracellular environment. The cell surface marker can be a protein, lipid, carbohydrate, or some combination of the three. The term "cell surface marker" includes naturally occurring molecules, molecules that are aberrantly present as the result of some disease condition, or a molecule that is attached to the surface of the cell.

By "lysis" is meant disruption of the cellular membrane. For the purposes of this invention, the term "lysis" is meant to include complete disruption of the cellular membrane ("complete lysis"), partial disruption of the cellular membrane ("partial lysis"), and permeabilization of the cellular membrane.

By "binding moiety" is meant a chemical species to which a cell binds. A binding moiety may be a compound coupled to a surface or the material making up the surface. Exemplary binding moieties include antibodies, antibody fragments (e.g., Fc fragments), oligo- or polypeptides, nucleic acids, cellular receptors, ligands, aptamers, MHC-peptide monomers or oligomers, biotin, avidin, oligonucleotides, coordination complexes, synthetic polymers, and carbohydrates.

By "permeabilization" is meant the disruption of the cellular membrane such that certain intracellular components are able to escape the cell, while other components remain inside the cell.

The term "chamber" is meant to include any designated portion of a microfluidic channel, e.g., where the cross-sectional area is greater, less than, or the same as channels entering and exiting the chamber.

Other features and advantages will be apparent from the following description, the figures, and the claims.

DETAILED DESCRIPTION OF THE INVENTION

Figure 1:
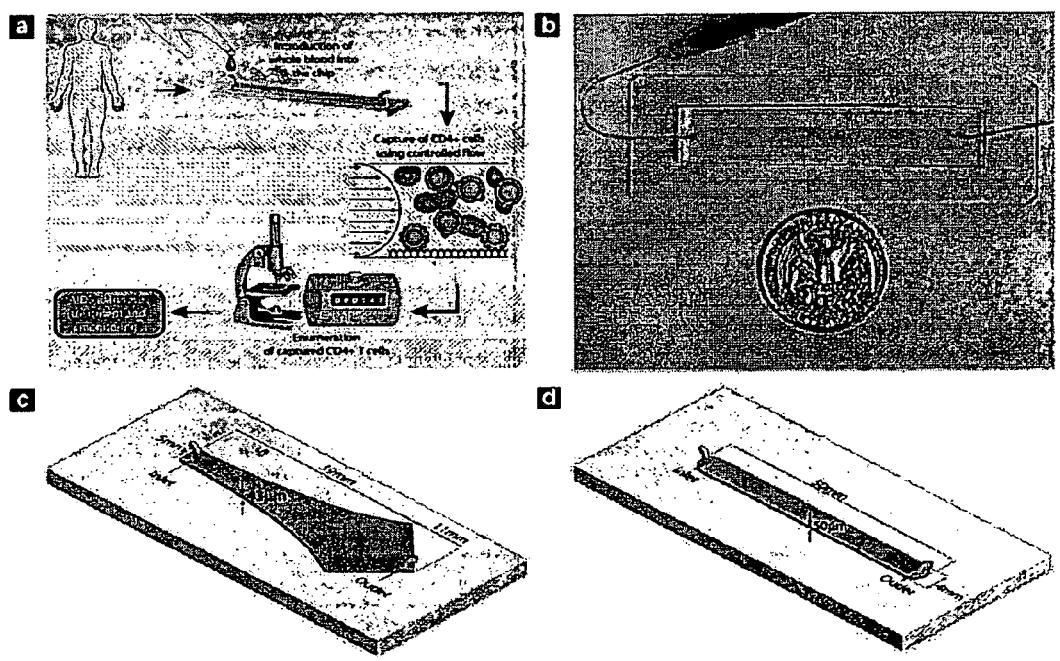
FIG. 1A is a diagram showing the operating procedure of a CD4 counting device.
FIG. 1B is a photograph of a cell counting device. Microfabricated PDMS devices with one inlet and one outlet were bound to glass slides to form closed chambers.
FIG. 1C is a diagram of the geometry of a Hele-Shaw device. The Hele-Shaw device offers linear variation of shear along its central line.
FIG. 1D is a diagram of the cell counting device of 1B. This device has a volume of 10 µL for sample volume metering.

In general the invention features methods, devices, and kits for the isolation of analytes (e.g., a cell). A sample containing a desired analyte is introduced into a microfluidic device containing moieties that bind the desired analyte. A shear stress is applied that is great enough to prevent binding of undesired analytes and low enough to allow binding of the analyte of interest. Once bound, the desired analytes can be analyzed (e.g., counted). The invention also features methods for determining a shear stress for isolating a desired analyte.

An exemplary embodiment of the invention provides a whole blood CD4+ T lymphocyte count assay using cell affinity chromatography in a microfluidic format. The device was functionalized with a specific antibody for affinity selection of target cells. Controlled shear stress applied in the microfluidic channel allows specific and efficient selection of CD4+ T cells versus monocyte and other white blood cells from a small volume sample, compatible with fingerprick collection. To perform CD4 counts, 10 μL of unprocessed whole blood is injected into the microfluidic channel at a controlled flow rate, and CD4+ T cell counts are determined as the number of all captured cells using a light microscope. The total assay time is less than 10 minutes.

One critical factor for accurate CD4 counting using this approach is the specificity of cell capture. To achieve this, we used cell affinity chromatography with immobilized antibodies, which are further blocked with BSA to reduce non-specific binding (Amiji and Park. J. Biomater. Sci. Polym. Ed. 4:217 (1993)). Because CD4 is also expressed on monocytes, we used shear stress as a secondary selection step to exclude monocytes. We found that CD4+ T lymphocytes and monocytes respond differently to shear stress on the functionalized device surface, as preferential binding of lymphocytes occurs in a window of 1-3 dyn cm$^{-1}$; by contrast, monocytes bind optimally at lower shear stresses. Selective binding within this window (1-3 dyn cm$^{-2}$) may be accounted for by two reasons. First, compared to lymphocytes, monocytes express about an order of magnitude less surface CD4, which reduces the chance of antibody-antigen interaction, especially under dynamic flow conditions (Lee et al. Proc. Natl. Acad. Sci. U.S.A. 96:5215 (1999)). Second, the larger size of monocytes increases the shear force exerted on individual cells (which is roughly proportional to the square of cell diameter), resulting in decreased binding efficacy. These two factors allow for differential binding of lymphocytes relative to monocytes. Controlled shear stress is also shown to be critical for efficient cell capture. The capture efficiency is further promoted by the elongated channel geometry, which increases the interaction time between target cells and the active surface area.

Within the optimal lymphocyte-binding window (1-3 dyn cm$^{-2}$), the shear force exerted on a cell 10 μm in diameter is ~8-25 pN. This is of the same order as the binding force of a single antibody-antigen pair. (Harada et al. Langmuir 16:708 (2000) and Hinterdorfer et al. Proc. Natl. Acad. Sci. U.S.A. 93:3477 (1996)) When the shear force is above this level, up to two orders of magnitude drop in cell adhesion is observed. This observation implies that when target cells come into contact with the surface, cell-substrate attachment is initiated by the formation of a single antibody-antigen interaction (Tissot et al. Biophys. J. 61:204 (1992)), and high membrane antigen density will favor the opportunity of such interaction. A somewhat surprising result was that the number of adherent cells also decreases when the shear is dropped below 1 dyn cm$^{-2}$. This decrease occurred when experiments were performed with whole blood, but not with lysed blood (data not shown). We believe that erythrocytes play an important role in the reduction of target cell binding at the low shear stress range. Erythrocytes have been known to induce margination of leukocyte flow in capillaries above certain flow rates. (Goldsmith and Spain. Microvasc. Res. 27:204 (1984) and Shevkoplyas et al. Anal. Chem. 77:933 (2005)) In our devices, margination is analogous to pushing the leukocytes to the floor and roof of the chamber. At low flow rates, the margination effect is not favored and, the erythrocytes in whole blood could occupy most of the functional surface and prevent antibody-antigen interactions. In lysed blood, cell-cell interaction is greatly reduced, and leukocyte settling is driven mainly by sedimentation, which does not decrease with reduced flow.

After the single channel device was optimized with blood from healthy donors (95%+ purity and 90%+ yield), its performance was tested with whole blood from HIV-infected subjects. We found a slight decrease in the device performance with samples from these subjects, which may be accounted for by several reasons. Interfering soluble factors in the serum of HIV-infected patients, such as soluble CD4, (Peakman et al. J. Infect. Dis. 165:799 (1992)) may compromise the yield of captured cells. Other soluble factors including cytokines, chemokines and immune complexes (Trial et al. J. Clin. Invest. 95:1690 (1995)) may influence behavior of blood cells. (Polo et al. AIDS. 13:447 (1999), Vonsydow et al. Aids Res. Hum. Retrov. 7:375 (1991), and Clerici et al. J. Clin. Invest. 91:759 (1993)). Leukocyte surface adhesion molecules may also be altered during HIV disease progression, (Trial et al. J. Clin. Invest. 95:1690 (1995) and Trial et al. J. Immunol. 173:2190 (2004)) which may lead to elevated non-specific binding in our device.

Changes on CD4+ T cell surfaces in HIV-infected subjects, such as down-regulation of CD4 receptors (Anderson et al. J. Virol. 67:4923 (1993)) and binding of gp120, (Thali et al. J. Virol. 66:5516 (1992)) might also reduce the receptor-antibody interaction and decrease yield. Thus, it was not surprising to see both purity and yield drop when samples from HIV-infected subjects were tested in the linear chamber device. Nonetheless, a linear relationship was observed for CD4 counts obtained by microchip and by flow cytometer in the clinically relevant range between 200 and 800 cells mL (Sato et al. Adv. Drug Deliv. Rev. 55:379 (2003)). Thus, the microfluidic device is useful for clinical decision making and disease monitoring in resource-limited settings. Further optimization of purity and yield should lead to even higher levels of accuracy.

The application of a microfluidic device for CD4 counting offers the advantages of reduced sample volume, decreased reagent consumption, low fabrication cost, and portability over conventional flow cytometric equipment. It uses a direct volumetric method and functions as a single platform. Moreover, no reagents need to be added to the assay, as required in single-platform flow cytometry and other proposed methods. Compared to the labor-intensive bead format assay and previously described miniaturized flow cell design, (Rodriguez et al. PLoS Med. 2:663 (2005)), the present invention this microfluidic CD4 counting device directly addresses the sample preparation challenge faced in most resource-poor settings. No sample preparation, such as lysing erythrocytes, pipetting, or mixing with antibody reagents is required, so the device serves as a self-contained system. No differentiation of monocytes from CD4+ T lymphocytes needs to be made during microscope-based counting.

We demonstrate a simple, quick, and inexpensive CD4+ T cell counting device based on microfluidic cell affinity chromatography operated under controlled shear stress. To our knowledge, this is the first device with which CD4 counts can be performed from a fingerprick sample of whole blood, without either sample processing or the addition of reagents. Minimum handling procedures, rapid operation, simple device and potential high-throughput detection makes this strategy a promising candidate for managing HIV patients in resource limited settings. We also note that CD4 counting is just one application for devices of this type. The demonstration of specific cell isolation with high efficiency using shear stress combined with cell affinity chromatography could be applied to a number of applications where specific and efficient cell isolation is required. In addition, applications of the invention are not limited to cells but are applicable to any analyte which can associate with a binding moiety and is subject to an appropriate amount of shear force. Such analytes include particles, e.g., magnetic, ceramic, or plastic, viruses, and molecular complexes, e.g., organelles and lipoprotein complexes.

I. METHODS OF ISOLATING AN ANALYTE

The invention features methods and devices for isolating cells and other analytes. The devices of the invention are microfluidic devices with at least one chamber, which may be a portion of a designated portion of a microfluidic channel or an entire channel. This chamber contains binding moieties specific for a desired analyte. Typically, the binding moieties are disposed on the walls of the channel, although additional structures, e.g., posts, may be included in the channel to increase the surface area. A sample containing the desired analyte is applied at a shear stress preferably low enough to allow binding of the desired analyte, but preferably great enough to prevent binding of undesired analytes, as described above for CD4+ cells.

In one embodiment, the chamber is coated with binding moieties that bind to a cell surface marker of a desired cell population. Through application of an appropriate shear stress, the methods of the invention result in the selective isolation of cells expressing these cell surface markers at a specific concentration. The applied shear stress is preferably great enough to prevent binding of undesired cells that contain the cell surface marker at a concentration lower than the desired population of cells and other non-specific binding interactions.

The methods of the invention result, for example, in the isolation of 50%, 60%, 70%, 80%, 90%, 95%, 99%, or 100% of the desired analyte, e.g., cells, in a sample while retaining, for example, less than 20%, 10%, 5%, or 1% of undesired analytes. In addition, while analytes that bind are described as being "desired" and analytes that do not bind are described as being "undesired," either type or both types of analyte may be of actual interest in a particular experiment. For example, the methods of the invention may be used to isolated analytes that either bind to the device or flow through the device.

At least two variables can be manipulated to control the shear stress applied to the channel: the cross sectional area of the chamber and the fluid pressure applied to the chamber. Other factors may be manipulated to control the amount of shear stress necessary to allow binding of desired analytes and to prevent binding of undesired analytes, e.g., the binding moiety employed and the density of the binding moiety in the channel.

The chamber may include multiple types of binding moieties (e.g., 1, 2, 3, 4, 5, or more). Multiple binding moieties may bind to the same or different analytes, and may be placed in the same or different chambers. For example, binding moieties to multiple cell surface markers that occur on a desired cell may be disposed in one chamber.

In another embodiment, the invention features chambers arranged in series, (e.g., 2, 3, 4, 5, or more chambers). In this embodiment, each chamber isolates one or more types of cells, which may or may not be the cells of interest. When multiple chambers are arranged in series, the shear stress applied to each of the chambers can be different (achieved for example by varying the cross sectional area of the chambers) or the shear stress can be the same. Also, when multiple chambers are arranged in series, each chamber can contain binding moieties that bind to different cell surface markers or the same cell surface markers. When the same binding moiety in employed in different chambers, the methods may be used to isolate, in series, analytes that have progressively lower amounts of substance to which the binding moiety binds.

The methods may also be employed to isolate various types of analytes in parallel, e.g., by passing aliquots of the same sample through separate devices or one device including multiple chambers in parallel. Different samples may also be assayed in parallel.

Devices used in the methods of the invention may be simply a microfluidic channel to which binding moieties are attached and which is capable of supporting fluid flow at the desired shear stress. The device geometry will be determined based on the assay. Devices may, or may not, include regions that allow for optical or visual inspection of the chambers. Fluid pumps capable of producing desired shear stress are also known in the art. Example of pumps include syringe pumps, peristaltic pumps, vacuum. Methods for coupling pumps to devices are known in the art. The device may be configured for substantially constant shear stress in any given chamber or variable shear stress in a given chamber. Exemplary devices are described herein.

Devices of the invention may be fabricated using techniques known in the art. The fabrication techniques employed will depend on the material used to make the device. Examples of fabrication techniques include molding, photolithography, electroforming, and machining. Exemplary materials include glass, polymers (e.g., polystyrene, silicones such as polydimethylsiloxane, epoxy, and urethanes), silicon and other semiconductors, and metals.

Binding moieties may be attached to chambers using methods known in the art. The method employed will depend on the binding moiety and the material used to construct the device. Examples of attachment methods include non-specific adsorption to the surface, either of the binding moiety or a compound to which the binding moiety is attached or chemical binding, e.g., through self assembled monolayers or silane chemistry.

Devices of the invention may be combined with fluids, pumps, and/or detectors. Devices may also be combined with reagents, e.g., lysis reagent, labeling reagents, and instructions for use, e.g., for disease diagnosis.

II. TARGET ANALYTES

Table 1 provides exemplary cell populations, cell surface markers appropriate for the methods and devices of the invention, and the corresponding shear stresses necessary to specifically isolate the indicated cells from a blood sample.

TABLE 1

| Blood cells isolated from whole blood | | | | |
|---|---|---|---|---|
| Optimal Shear [dyne/cm$^2$] | Wash [dyne/cm$^2$] | Capture molecule | Purity* | Yield |
| Neutrophil 0.4 | 1.5 | Anti-CD66 | 93% | 80% |
| Monocyte 0.3 | 0.7 | Anti-CD14 | 93% | |
| Lymphocyte 1.3-1.7 | 3 | Anti-CD4 Anti-CD8 | 99% | 80% |
| Circulating tumor cells 8-9 | 35 | Anti-EpCAM | 80%# | 60% |
| Neutrophils 1-7 | — | E, P Selectins | 70% | 80% |

TABLE 1-continued

| Blood cells isolated from whole blood | | | | |
|---|---|---|---|---|
| Optimal Shear [dyne/cm$^2$] | Wash [dyne/cm$^2$] | Capture molecule | Purity* | Yield |
| HIV-specific T cell 0.082 | N/A | HLA A2-SL9 pentamer | >99% | N/A |
| Any disease specific T cell 0.07-0.1 | | Pentamer | | |

*blood from healthy donor
blood from patients with cancer stage III-IV

Additional exemplary cell surface markers appropriate for the methods and devices of the invention are set forth in Table 2. Cell types also include disease-specific T cells, either CD4+ or CD8+, which can be isolated using MHC-peptide monomers, tetramers, or pentamers as the binding moiety. Shear stresses appropriate for isolating cells expressing the cell surface markers in Table 2 can be determined as described. In addition the cells set forth in Table 2, the invention is also useful, for example, for isolating human and animal pathogens (e.g., protists, bacteria, and fungi), fetal cells (e.g., nucleated red blood cells, amniocytes, and trophoblasts), stem cells (embryonic or adult), sickle cell red blood cells, and white blood cells.

TABLE 2

| Cell Surface Markers | | |
|---|---|---|
| Desired Cell | Binding Moiety | Cross reactivity |
| Dendritic cells | Anti-CD83 | Weak cross reactivity with lymphoblastoid cell lines and with some germinal center B cells |
| Monocyte | Anti-CD14 antibody | weakly on the surface of granulocytes; also expressed by most tissue macrophages |
| Tuberculosis sensitive CD8 T cell | P MHC Pentamer A2-SL9 | Weak cross reactivity with other MHC class II molecules |
| Platelets | Anti-CD41 | Less abundant expression on Megakaryocytes |
| Endothelial progenitor cells | Anti-CD34 | Less expressed on small-vessel endothelial cells, embryonic fibroblasts |
| Epithelial progenitor cells | Anti-CD133 | Hematopoietic cells |
| Mesenchimal progenitor cells | Bone morphogenetic protein receptor (BMPR) | Stromal cells, fibroblasts |

In order to determine the optimum shear stress to isolate cells containing a desired cell surface marker, a sample of cells may be applied to a Hele-Shaw chamber (e.g., the device set forth in FIG. 1C) designed based on the equations derived by Usami et al. (Murthy et al. Langmuir. 20:11649 (2004) and Usami et al. Ann. Biomed. Eng. 21:77 (1993)). The shape of the chamber of this device is such that the shear stress along the axis of the chamber decreases linearly along the chamber length. The Hele-Shaw devices can be used to determine the dynamics of cell attachment to microfluidic devices because multiple shear rates can be obtained in each flow chamber without changing the inlet flow rates. By identifying the narrowest location along the axis of the Hele-Shaw chamber where the desired cells bind, the corresponding shear rate can be calculate using the equations cited above.

III. BINDING MOIETIES

Binding moieties useful in the devices and methods of the invention include antibodies, antibody fragments (e.g., Fc fragments), oligo- or polypeptides, nucleic acids, cellular receptors, ligands, aptamers, MHC-peptide monomers or oligomers, biotin, avidin, oligonucleotides, coordination complexes, synthetic polymers, and carbohydrates.

IV. METHODS OF USE

In addition to methods of isolating various analytes from a sample, the invention provides methods in which the analyte isolated may be used to provide additional information. In particular, cells isolated using the methods and devices of the invention can be further assayed using additional methods of the invention. In one embodiment, cells that are isolated using the methods and devices of the invention are counted. Cells can be counting by any method known in the art, including optical, e.g., visual inspection, automated counting, microscopy based detection, and FACS, and electrical detection, e.g., Coulter counters. Counting of the cells, or other analytes, isolated using the methods and devices of the invention can be useful for diagnosing diseases, monitoring the progress of disease, and monitoring or determining the efficacy of a treatment. Cell, or other analyte, counting may also be of use in non-medical applications, e.g., for determination of the amount, presence, or type of contaminants in environmental samples (e.g., water, air, and soil), pharmaceuticals, food, or cosmetics.

Many diseases are characterized by abnormal levels of cells containing certain cell surface markers (e.g., see Table 2). Also cells infected with certain pathogens often express unique cell surface markers, unique combinations of cell surface markers, or express cell surface markers at abnormal levels.

In another embodiment, cells isolated using the methods and devices of the invention can be lysed, and one or more properties of the cells, or portions thereof, can be measured. Examples of biological properties that can be measured in isolated cells include mRNA expression, protein expression, and DNA quantification. Additionally, the DNA of cells isolated by the methods of the invention can be sequenced, or certain sequence characteristics (e.g., polymorphisms and chromosomal abnormalities) can be identified using standard techniques, e.g., FISH or PCR. The chemical components of cells, and other analytes, may also be assayed after isolation.

V. EXAMPLES

Example 1

Isolation of CD4+ T Lymphocytes

Materials

3-Mercaptopropyl trimethoxysilane was purchased from Gelest (Morrisville, Pa.). Ethanol (200 proof), glass coverslips (35×60 mm, no. 1), hemacytometer and microslide fieldfinder were obtained from Fisher Scientific (Fair Lawn, N.J.). For chamber fabrication, SU-8 photoresist and developer were obtained from MicroChem (Newton, Mass.); silicone elastomer and curing agent were obtained from Dow Corning (Midland, Mich.). Phosphate buffered saline (PBS) was obtained from Mediatech (Herndon, Va.). Lyophilized bovine serum albumin (BSA) was obtained from Aldrich Chemical Co. (Milwaukee, Wis.). The coupling agent GMBS (N-γ-maleimidobutyryloxy succinimide ester) and NeutrAvidin were obtained from Pierce Biotechnology (Rockford, Ill.). Biotinylated mouse anti-human anti-CD4 (clone 13b8.2) was purchased from Beckman Coulter (Somerset, N.J.). Biotinylated mouse antihuman anti-CD36 (clone SMO) was obtained from Ancell (Bayport, Minn.). Alexa Fluorl 488-conjugated mouse antibody to human CD4 (AF488-anti-CD4, clone 289-14120), Alexa Fluorl 647-conjugated mouse antibody to human CD3 (AF647-anti-CD3, clone 289-13801) and 4'-6-diamidino-2-phenylindole (DAPI) were obtained from Molecular Probes (Eugene, Oreg.). Phycoerythrin (PE)-conjugated mouse antihuman CD14 monoclonal antibody (PE-anti-CD14, clone M5E2) was purchased from BD Bioscience (San Diego, Calif.). Paraformaldehyde was obtained from Electron Microscopy Sciences (Hatfield, Pa.).

Chamber Design and Fabrication

Two types of microfluidic devices were used in this work. The first one was the Hele-Shaw chamber (FIG. 1C) designed based on the equations derived by Usami et al. (Murthy et al. Langmuir. 20:11649 (2004) and Usami et al. Ann. Biomed. Eng. 21:77 (1993)). The shape of the chambers is such that the shear stress along the axis of the chamber decreases linearly along the chamber length. The fabricated flow chambers were 43±1 μm in height with inlet width and total length of 5 mm and 50 mm, respectively. The Hele-Shaw devices were used to study the dynamics of lymphocyte attachment to microdevices using healthy donor blood, since multiple shear rates can be obtained in each flow chamber without changing the inlet flow rates. The second type of device was a straight flow channel (FIG. 1d), which provides a constant shear stress along the channel length and has a footprint of 2 $cm^2$. The width, length and height of the channel were 4 mm, 51 mm and 50±1 μm respectively. The straight channel device was used for actual cell capture and counting experiments, using the operating shear stress determined from the Hele-Shaw experimental data. The devices were fabricated in PDMS and bonded permanently to clean glass cover slips using standard clean room techniques. (Murthy et al. Langmuir. 20:11649 (2004) and Usami et al. Ann. Biomed. Eng. 21:77 (1993))

Surface Modification

Freshly fabricated devices were modified using the method described previously. (Murthy et al. Langmuir. 20:11649 (2004) and Usami et al. Ann. Biomed. Eng. 21:77 (1993)) Briefly, the chambers were pretreated with 4% (v/v) solution of 3-mercaptopropyl trimethoxysilane in ethanol for 30 min at room temperature, followed with incubating the chambers with 0.01 mmol mL (Sato et al. Adv. Drug Deliv. Rev. 55:379 (2003)) GMBS in ethanol for 15 min at room temperature. Afterwards, NeutrAvidin was immobilized to GMBS by incubating the chamber surfaces with 10 mg $ml^{-1}$ NeutrAvidin solution in PBS for at least 1 h at 4° C. Finally, 10 mg $mL^{-1}$ (ibid) biotinylated anti-CD4 solution in PBS containing 1% (w/v) BSA and 0.09% (w/v) sodium azide was injected to react at room temperature for 15 min. After each step, the surfaces were rinsed with either ethanol or PBS, depending on the solvent used in the previous step, to flush away unreacted molecules.

Study Subjects and Blood Preparation

Healthy HIV-negative and HIV-infected subjects were recruited from the Massachusetts General Hospital (MGH) in Boston. All subjects provided written informed consent. Samples of 5 mL of peripheral blood were collected by venipuncture in either heparin or EDTA Vacutainer collection tubes (Becton Dickinson). All samples were run on the microfluidic devices on the day of blood collection. Parallel measurement of CD4 counts of the HIV infected subjects were taken through standard clinical laboratory operating procedures, as described previously. (Rodriguez et al. PLoS Med. 2:663 (2005)) Briefly, patient samples were processed in the hospital clinical laboratory using standard 4-color flow cytometry on a Becton Dickinson FACSCalibur, using the MultiTEST reagents and TruCOUNT beads and analyzed using MultiSET software to obtain CD4 counts.

Microfluidic Flow Experiments

In experiments performed to develop the prototype microdevice, 300 µl of unprocessed whole blood from healthy donors was introduced into the Hele-Shaw chambers at the desired shear rates (5-40 µl min$^{-1}$) using a syringe pump (Harvard Apparatus PHD 2000, Holliston, Mass.). The volume of whole blood was chosen such that cell adhesion on the surfaces reached a pseudo-steady state, where no significant increase of captured cells was observed as determined by both examining the number of cells adhered on the surfaces and the blood samples collected from the device outlet. Immediately after sample delivery, PBS containing 1% BSA (w/v) and 1 mM EDTA was flowed through the chamber at 40 µL min$^{-1}$ for 5 min to rinse off the unbound cells. The cells were then fixed on the surfaces by incubating with 1% paraformaldehyde, followed with incubating with an antibody mixture containing AF647-anti-CD3/AF488-anti-CD4/PE-anti-CD14 for 15 min. After rinsing off the unbound antibody with PBS containing 1% BSA (w/v) and 1 mM EDTA, the number of adhered cells were counted by placing a field finder under the chambers and counting cells at select points along the device axis using an inverted microscope (Nikon Eclipse TE2000, Nikon, Japan). Monocytes were identified by staining with antibody to CD14, CD4+ T cells were recognized by CD3+/CD4+/CD14− staining, and the total number of adherent nucleated cells were determined by staining with DAPI or direct observation under the phase contrast microscope. For each point, three measurements were made, corresponding to three 1 mm$^2$ squares in that vicinity, and averaged. Images were obtained at 10$^6$ magnification using fluorescein, rhodamine, and Cy5 excitation/emission filters. DAPI staining was performed afterwards by incubating the surface-attached cells with 300 nM DAPI in PBS at room temperature for 5 min and rinsing with PBS. The cells were counted either manually or using Image J software (http://rsb.info.nih.gov/ij/). To avoid competitive binding between the capture antibody and the labelling antibody, CD4 antibodies were selected to bind to different epitopes.

In experiments performed to test the CD4 cell counting device, 10 µl of whole blood from healthy donors or HIV infected subjects was flowed into linear chambers at the desired flow rates (1-20 µl min$^{-1}$). After rinsing at a flow rate of 20 µl min$^{-1}$, cells adhered to the surface were stained and counted using similar procedures to the ones described above for Hele-Shaw devices. Sample flow-through and rinse buffer were collected from the outlet of the device into Eppendorf tubes and centrifuged to concentrate the cells for flow cytometry.

Flow Cytometry Analysis

In order to confirm the efficiency of the devices in depleting target cells from whole blood, aliquots of samples before and after passage through the linear chamber devices were collected and analysed using standard flow cytometry to quantify the percentage of CD4+ T cells. The flow cytometric measurements were performed on a FACSCalibur (Beckton Dickinson Immunocytometry System (BDIS), San Jose, Calif.) instrument using BD CellQuest Pro Software. The capture efficiency, or yield of the device was estimated from the ratio of the percentage of CD3+ CD4+ T cells in samples collected before and after passing through the microfluidic device.

Statistics and Data Analysis

Figure 2:
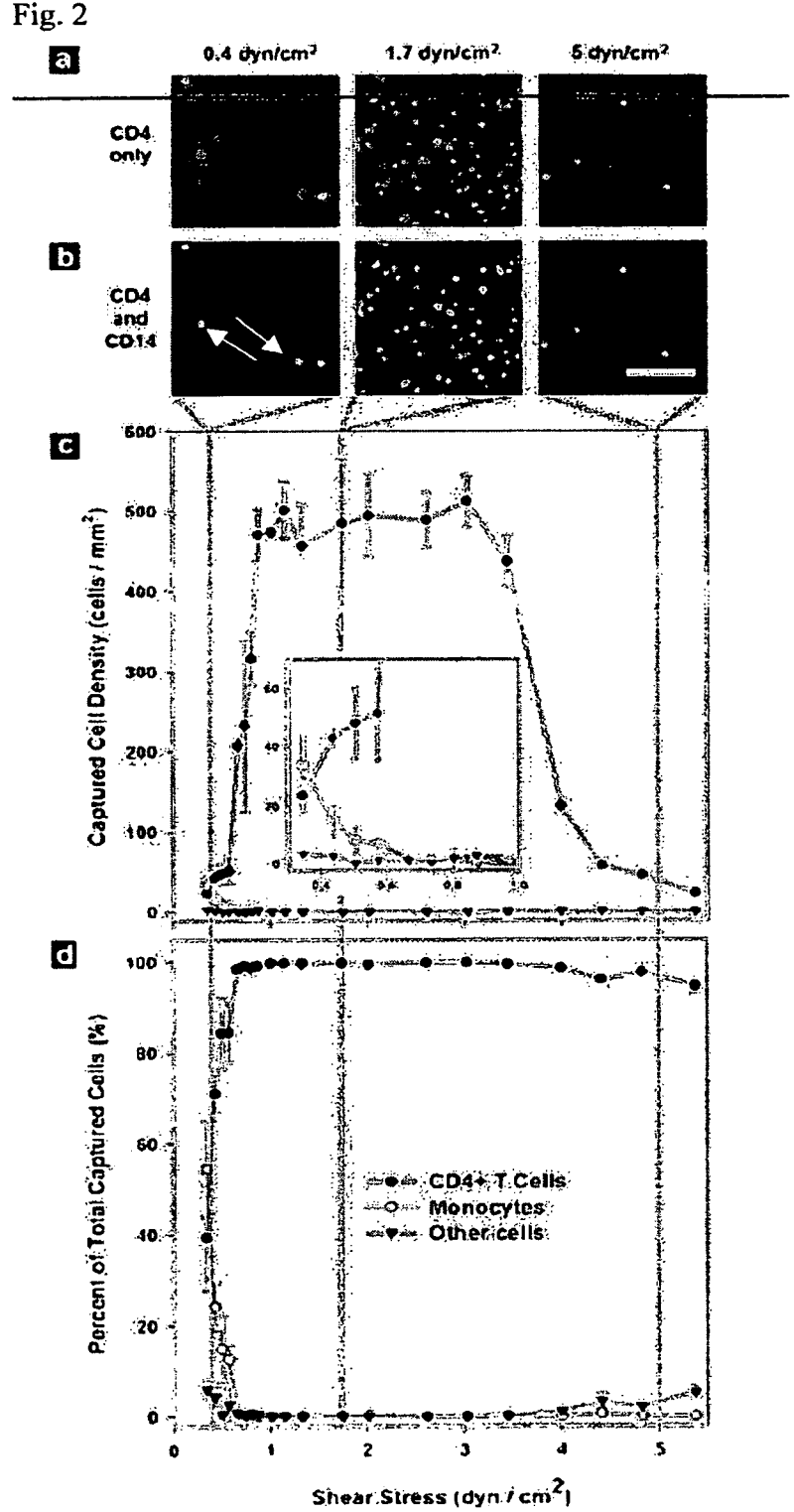
FIG. 2A is a series of photomicrographs of cells captured in a Hele-Shaw chamber at locations corresponding to shear stresses of 0.4 dyn cm$^{-2}$ (left), 1.7 dyn cm$^{-2}$ (middle) and 5 dyn cm$^{-2}$ (right). The image was created by overlapping a phase contrast photograph and the corresponding fluorescence photograph.
FIG. 2B is a series of photomicrographs of captured cells after CD4 (arrows) and CD14 staining at the shear stresses conditions as described above. Both lymphocytes (CD4+ CD14−) and monocytes (CD4+CD14+) were captured at the shear stress of 0.5 dyn cm$^{-2}$, but pure lymphocytes were captured at two higher shear stresses. (Bar: 100 mm)
FIG. 2C is a graph showing adhesion of CD4+ T cells (solid circles), monocytes (empty circles) and other cells (solid triangles) in response to shear stress. Differentiated capture of monocytes and lymphocytes in response to shear was observed. A shear stress window between 1 and 3 dyn cm$^{-2}$ was optimal for CD4+ T cell adhesion, while monocytes adhesion drops significantly above 0.7 dyn cm$^{-2}$ (inset). The adhesion of other cells is minimal in the whole range of tested shear stress. Each data point was repeated in 3 devices spanning different shear stress ranges; error bars represent standard deviations in measurements within each experiment.
FIG. 2D is a graph showing composition of the surface captured cells as a function of shear stress. When shear stress is above 0.7 dyn cm$^{-2}$, 95% of the surface captured cells are CD4+ T cells (solid circles). The purity of these cells drops quickly to less than 50% when shear stress drops below 0.7 dyn cm$^{-2}$. Each data point was repeated in 3 devices spanning different shear stress ranges; error bars represent standard deviations in measurements within each experiment.
Figure 3:
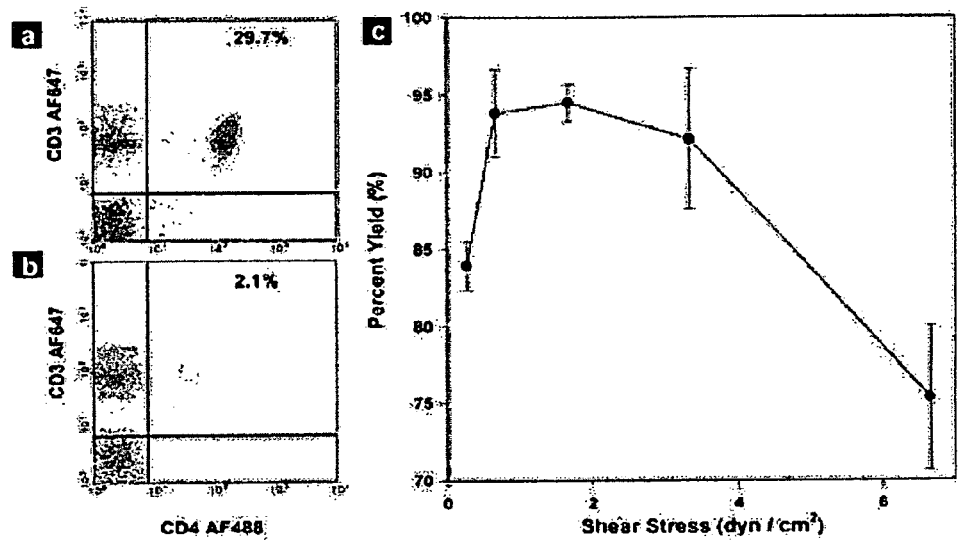
FIG. 3A is a graph showing flow cytometric analysis of a blood sample before CD4+ T cell isolation. The CD4+ T cells (CD3+CD4+) compose 29.67% of all lymphocytes.
FIG. 3B is a graph showing flow cytometric analysis of the same blood sample after CD4+ T cell capture in the device. The composition of the target cells in the sample flow through dropped to 2.13% of all lymphocyte population after device capture. Ten microliters of whole blood were injected into the linear device at a shear stress of 1.7 dyn cm$^{-2}$. Cells were acquired in the gated lymphocyte population, and the quadrants were set up with an isotype matched control.
FIG. 3C is a graph showing percent yield of captured cells as a function of shear stress calculated from flow cytometric analysis. Nearly 95% of the target cells can be isolated from whole blood using shear stress in the range of 1 to 3 dyn cm$^{-2}$. The yield quickly drops to less than 85% out of this range. Each data point was repeated in at least 3 devices. The error bars represent standard deviations in measurements within each experiment.
Figure 4:
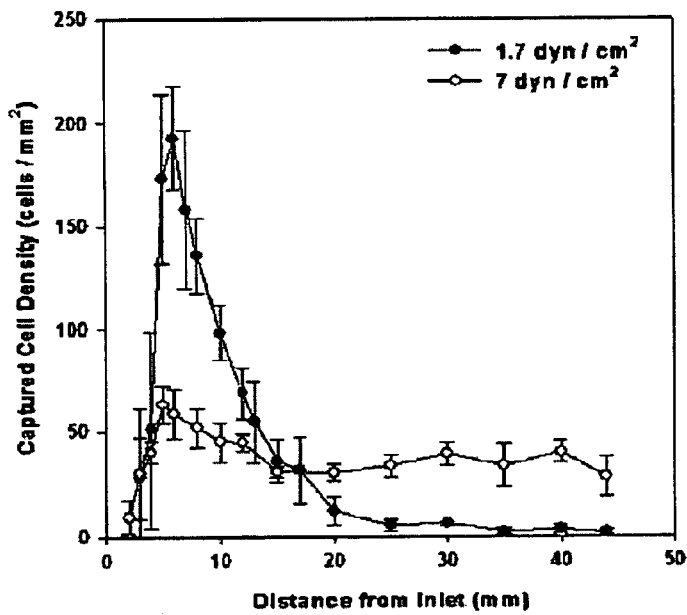
FIG. 4 is a graph showing capture cell density as a function of distance from inlet using the linear cell capture chamber at two shear stresses. At 1.7 dyn cm$^{-2}$ (solid circle, yield nearly 95%), captured cell density reaches maximum near the sample inlet. By contrast, at 7 dyn cm$^{-2}$ (empty circle, yield 75%), the distribution of cells is fairly uniform along the device. The experiments were performed using 10 µL of whole blood from healthy subjects. Each data point was repeated in at least 3 devices. The error bars represent standard deviations in measurements within each experiment.

The experiments performed with blood from healthy HIV negative subjects were repeated in at least 3 different devices at each condition. Data shown in FIGS. 2, 3 and 4 represent cell counts or flow cytometric measurements averaged over these devices, and each error bar represents the standard error of the mean.

Results

Development of a Simple Device for CD4+ Cell Separation from Whole Blood Using Affinity Isolation Chemistry Using device simplicity and accuracy as our key objectives, we identified two key factors in our design criteria: the specificity (purity) and efficiency (yield) of CD4+ T cell capture in a label-free microfluidic device. We first tested how specific an anti-CD4-immobilized, BSA-blocked surface is in capturing CD4-presenting cells. FIG. 2A shows representative overlapped phase contrast images and anti-CD4 stained fluorescent images of cells from whole blood obtained from a healthy, HIV-negative subject and adherent to anti-CD4 functionalized surfaces. As shown, almost all captured cells (density ~50-500 cells mm$^{-2}$) stained positively for surface CD4 antigen. A control device lacking a specific cell capture antibody demonstrated 1-2 orders of magnitude lower cell attachment from whole blood (density, 5 cells mm$^{-2}$). Thus, a surface functionalization scheme appeared successful in exclusively capturing CD4-presenting cells from unlabeled whole blood samples.

Monocyte Versus CD4+ T Lymphocyte Adhesion from Whole Blood

In circulating cells, CD4 molecules are present on both lymphocytes and monocytes, which cannot be differentiated by immobilized anti-CD4 alone. This can be observed in FIG. 2B, where some of the CD4-presenting cells (stained green) also stain with the monocyte marker CD14. Thus, for the purpose of enumerating CD4+ T cells alone, a secondary selection mechanism has to be used to exclude monocyte binding. We used shear stress for this purpose, considering the lower CD4 expression level on monocytes relative to CD4+ T cells, as well as their size differences. To study the effect of shear stress on monocyte and lymphocyte adhesion, we used antibody-functionalized Hele-Shaw devices (FIG. 1C), which allows for an analysis of cell adhesion over a range of shear stresses in a single experiment. (Murthy et al. Langmuir. 20:11649 (2004) and Usami et al. Ann. Biomed. Eng. 21:77 (1993))

FIG. 2C compares the adhesion profiles of monocytes (empty circles) and CD4+ lymphocytes (solid circles) within a shear stress range of 0.15 to 5 dyn cm$^{-2}$. Maximum adhesion of CD4+ lymphocytes occurs in a shear stress window between 1 and 3 dyn cm$^{-2}$. Within this region, roughly 500 cells adhered per square millimeter of area. The adhesion of CD4+ T cells decreases rapidly outside of this shear stress window. In contrast to lymphocyte adhesion on the anti-CD4 surface, monocytes have a different dependence on shear stress (inset in FIG. 2C). Monocyte adhesion drops from about 40 cells mm$^{-2}$ to around 5 cells mm$^{-2}$ when the shear stress increases from 0.3 to 0.7 dyn cm$^{-2}$, and remains below 5 cells mm$^{-2}$ when the shear stress is above 0.7 dyn cm$^{-2}$. We also plotted the number of other cells (the total number of adherent cells minus monocytes and CD4+ T cells) adherent to the anti-CD4 surface (solid triangles in FIG. 2C). The non-specific cell number remained at a constant low level (<5 cells mm$^{-2}$) throughout the tested shear stress range.

When the cell composition on the device surface is plotted (FIG. 2D), we observe that purity of surface captured CD4+ T lymphocytes is more than 95% when the shear stress is above 0.7 dyn cm (Chovan and Guttman. Trends Biotechnol. 20:116

(2002)). Purity drops at shear stress below 0.7 dyn cm$^{-2}$, due mainly to the adhesion of monocytes under the low shear condition; purity also drops slightly above 4 dyn cm$^{-2}$. Thus, shear stress is a powerful tool to differentiate specific adhesion of CD4+ T lymphocytes and monocytes.

Development of a Cell Counting Device and Determination of Capture Efficiency

In the initial experiments, we demonstrated highly selective capture of CD4+ T cells using a monoclonal antibody functionalized surface operated under differential shear stress. Next, we designed a straight channel device for efficient isolation of CD4+ T lymphocytes under fixed shear stress within the shear stress range optimized for pure CD4+ T cell capture without contaminating monocytes (FIG. 1D). This simple device had an internal volume of 10 μL, which serves as a sample volume metering mechanism. The 10 μL volume allows for convenient delivery of a small-volume sample obtained from a study subject, and sufficient sample size for statistically valid cell counts. The elongated chamber design increases the interaction time of blood with the functional surface.

We injected 10 μL of whole blood at shear stresses ranging from 0.2-7 dyn cm$^{-2}$ into the linear device, collected samples before and after flow through the chamber, and analyzed them by flow cytometry to study the capture efficiency within this device. Representative quadrant analysis data from the lymphocyte window of blood samples before and after passage through the device at a shear stress of 1.7 dyn cm$^{-2}$ are shown in FIGS. 3A and 3B. In this representative experiment, CD4+ T lymphocytes (CD3+ CD4+) comprised 29.7% of all lymphocytes entering the microfluidic channel (FIG. 3A); after selective capture, this fraction dropped to 2.1% of lymphocytes exiting the device (FIG. 3B), indicating retention of more than 90% of the target CD4+ T cells within the device at this shear stress. Similar experiments were performed at various shear stresses to study the effect of shear stress on capture efficiency (or yield) of CD4+ T cells in the linear device (FIG. 3C). We observed that a shear stress window of 1-3 dyn cm$^{-2}$ was optimal for efficient CD4+ T cell capture in the linear chamber, matching the results obtained using the Hele-Shaw chamber (FIG. 2C). Within this shear stress window, nearly 95% of the CD4+ T lymphocytes were isolated with purity greater than 95%. Outside of this window, capture efficiency quickly dropped to 70-80%, along with a decrease in purity (FIG. 3C). When we evaluated cell distribution in devices operated at two shear stresses in and out of the optimal window, we observed differences that help to explain the mechanism for their distinctive capture efficiency (FIG. 4). At a shear of 1.7 dyn cm$^{-2}$, which yielded 95% target cells, a narrow cell density peak of around 200 adherent cells mm$^{-2}$ was seen within 10 mm from the device inlet; this density quickly dropped below 20 cells mm$^{-2}$ at greater distances from the inlet. In contrast, at a less efficient shear of 7 dyn cm$^{-2}$, surface-captured cells remain at a relatively constant, low density throughout the length of the chamber. Thus, controlled shear flow in a simple, anti-CD4 functionalized device promotes efficient and specific CD4+ T cell capture.

Figure 5:
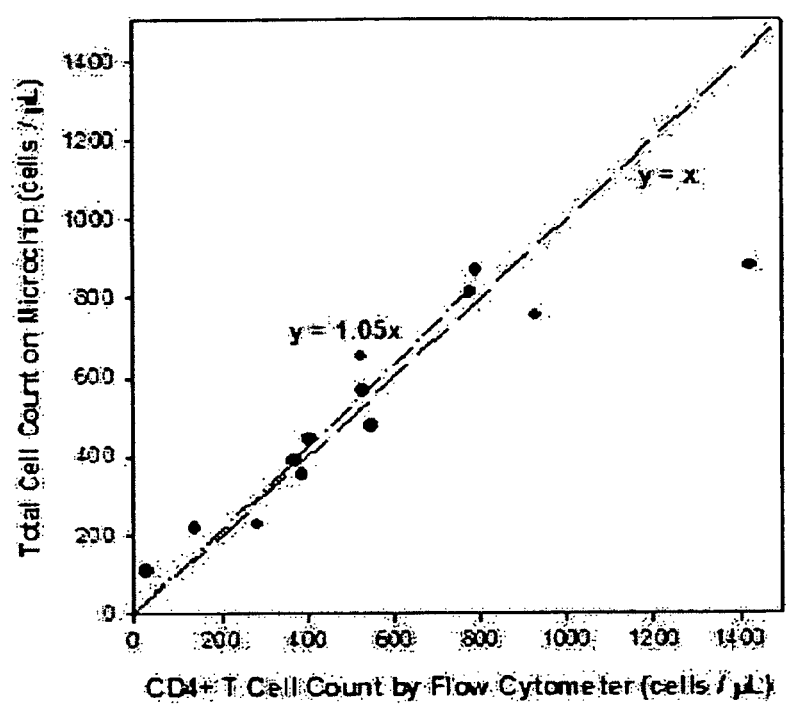
FIG. 5 is a graph showing cells counted on the microfluidic chip as a function of CD4+ T cell count by flow cytometer using whole blood from 13 HIV+ adult subjects. A linear regression of the experimental data for absolute CD4 counts under 800 cells mL$^{-1}$ (n=11) indicates good correlation between the two measurements (dash-dot line). The dashline represents an ideal 1:1 correlation between the two.

CD4 Counts from HIV-Infected Subjects Using Optimized, Simple Microfluidic Devices After determining the optimal conditions for the device using blood from healthy donors, we next tested the devices using samples obtained from HIV+ adult subjects. A ten-microliter sample of blood was introduced for 2 min at 5 μL min$^{-2}$, which corresponds to a shear stress of 1.7 dyn cm$^{-2}$. Next, buffer was introduced at 20 μL min$^{-2}$, which corresponds to a shear stress of ~7 dyn cm$^{-2}$, to remove monocytes and non-specific cells. CD4 counts were then determined from the total number of adherent cells, counted manually under a phase contrast microscope; total assay time was under 10 min. We compared these CD4 counts from our microdevice with results obtained from samples processed in parallel by flow cytometry (FIG. 5). For 13 adult study subjects with CD4 counts ranging from 26 to 1428 cells μL$^{-1}$ by flow cytometry, our results show a close correlation between the two methods at CD4 counts up to 800 cells μL$^{-1}$ (n=11, R$^2$=0.93) respectively. At CD4 counts above 800 cells μL$^{-1}$, the microdevice cell counts are significantly lower than those obtained by flow cytometry, which likely reflects saturation of cell binding within the chamber.

Figure 6:
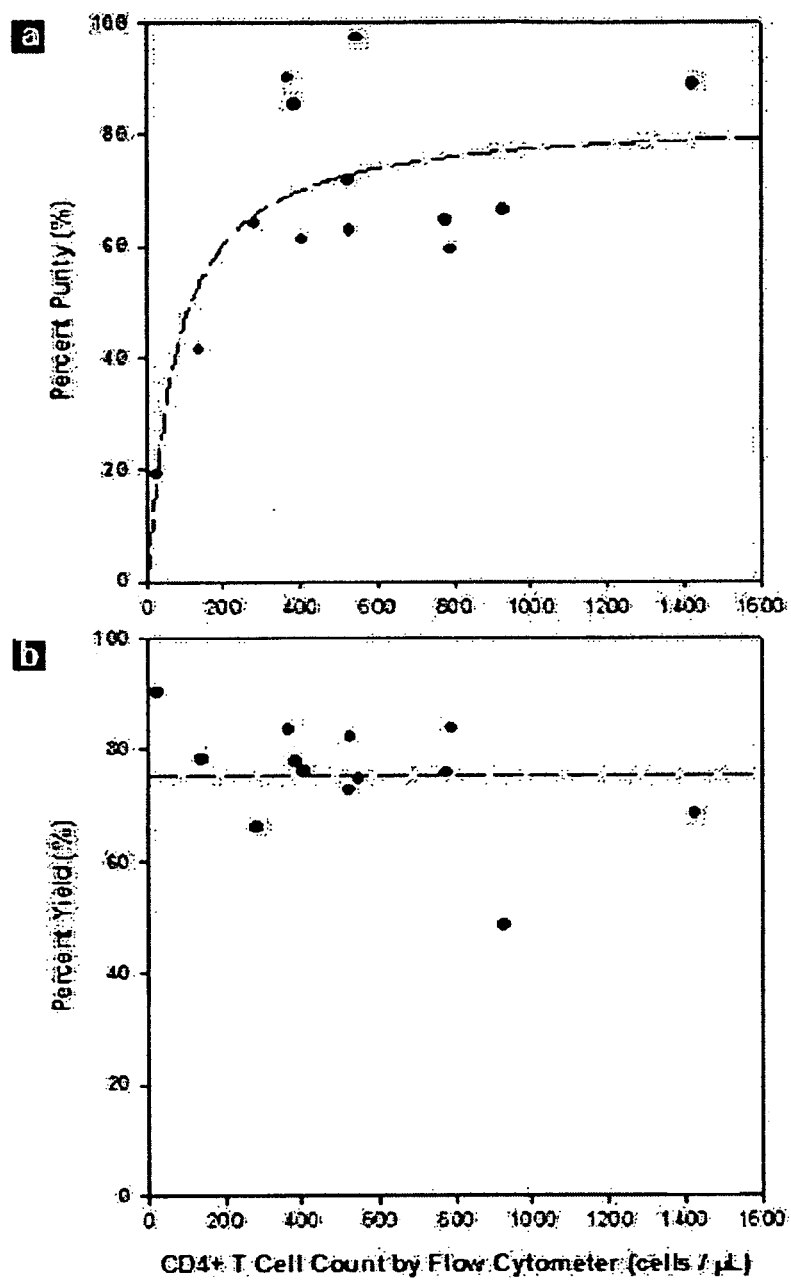
FIG. 6A is a graph showing purity of the surface captured CD4+ T cells as a function of the absolute CD4 counts. Purity was above 60% and fairly consistent for absolute CD4 counts greater than 200 cells $\mu L^{-1}$.
FIG. 6B is a graph showing yield of CD4+ T cells within the linear device as a function of the absolute CD4 counts. Fairly consistent yield was observed for absolute CD4 counts up to 800 cells $\mu L^{-1}$. The dashed lines are drawn as a visual guide.

To confirm these findings, we assessed the purity and yield of CD4+ T cells in the linear device using whole blood from HIV-infected subjects (FIGS. 6A and B). Purity (or capture specificity) was calculated by taking the ratio of CD4+ T cells (CD3+CD4+) to the total number of captured cells (DAPI+); yield (or capture efficiency) was defined as the ratio of captured CD4+ T cells to the sum of captured CD4+ T cells plus those lost in the flow through. For the 13 study subjects, a consistent yield (>75%) was observed for CD4 counts up to 800 cells μL$^{-1}$; the yield started to drop for subjects with higher absolute CD4 counts. Purity ranged from 60-90% for CD4 counts above 200 cells μL$^{-1}$. When the absolute CD4 count is below 200 cells μL$^{-1}$, poorer capture specificity was observed (20-50%). Nevertheless, a clear cutoff was observed for CD4 counts around 200 cells μL$^{-1}$, which is used clinically to discriminate relevant CD4 count thresholds. We also observed that >90% of the non-target cells are monocytes (data not shown), which in the context of HIV infection may be more adherent to an anti-CD4 functionalized surface than monocytes from uninfected blood.

Example 2

Arrangements of Capture Chambers

Figure 7:
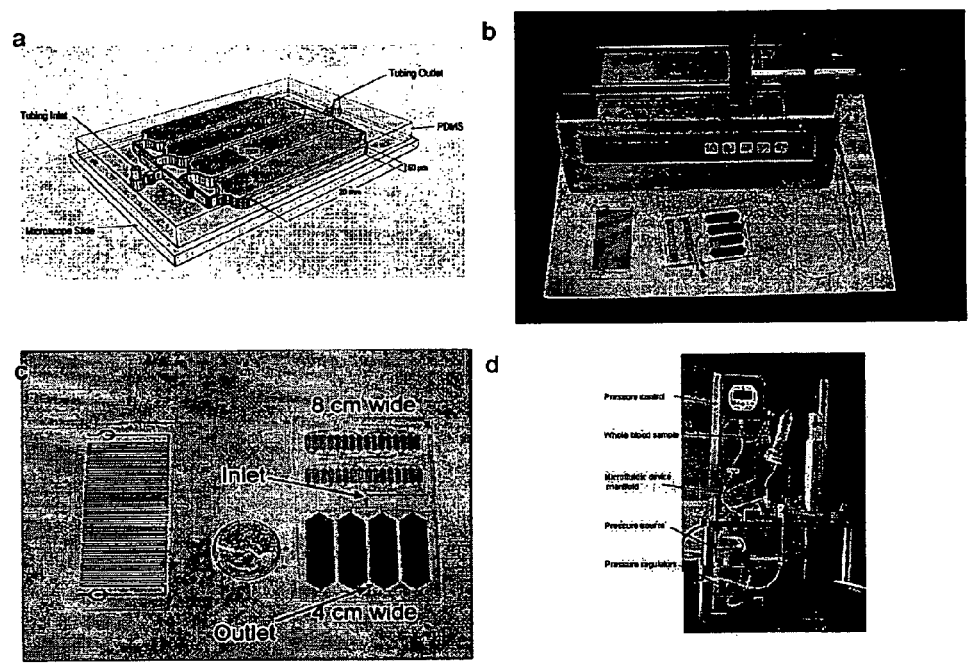
FIG. 7A is a schematic of the microfluidic device with multiple parallel chambers for cell isolation.
FIGS. 7B and 7C are photographs of examples of devices connected to a syringe pump.
FIG. 7D is a photograph of a microfluidic station using pressure driven flow to automate the isolation of cells from whole blood.
Figure 8:
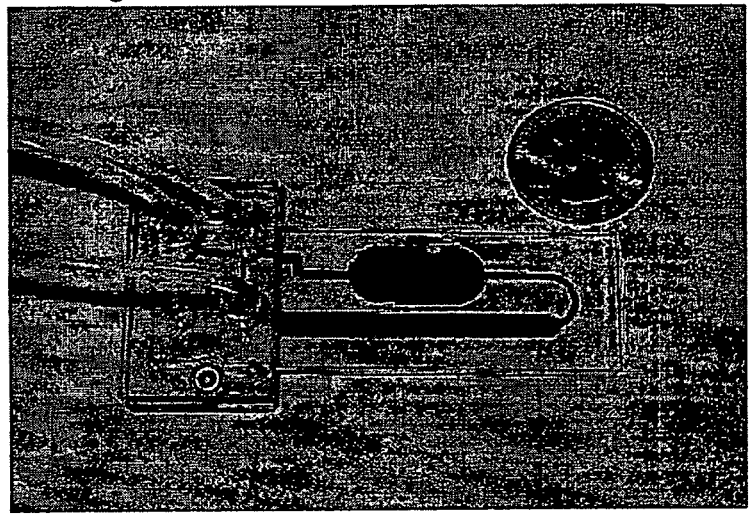
FIG. 8 is a photograph of a Microfluidic Cell Isolation Device with two cell-capture chambers in series. The first chamber (top) captures and depletes contaminating cells, increasing the purity of the cells captured inside the second chamber.
Figure 9:
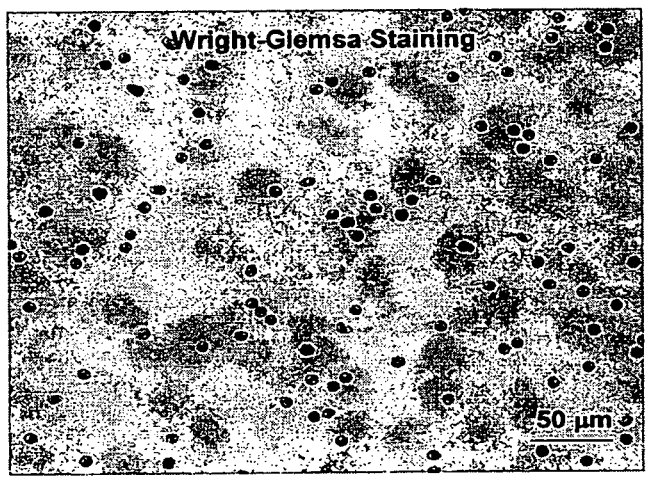
FIG. 9 is a photomicrograph of captured CD66b+ granulocytes treated with Wright-Giemsa stain. No significant platelet contamination is observed.
Figure 10:
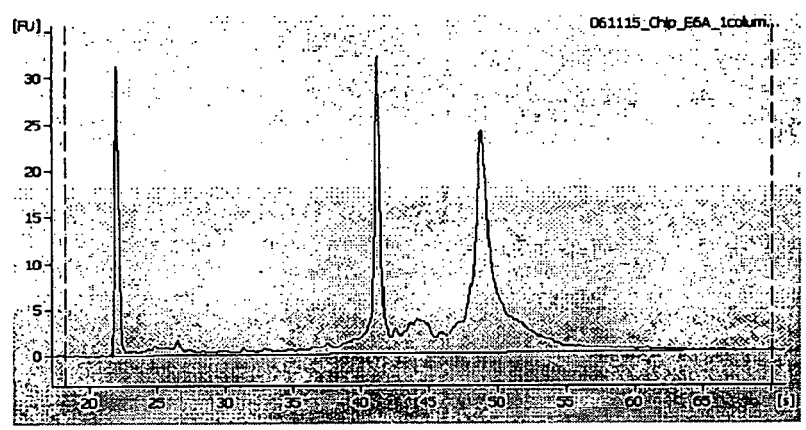
FIG. 10 is a graph showing typical electrophoresis of the RNA isolated from neutrophils isolated using the microfluidic chambers. A total of 33 ng total RNA was isolated from neutrophils isolated from 100 μL of blood. The quality of RNA is very good indicting the compatibility of cell capture with RNA extraction techniques.

A flat microfluidic chamber (FIG. 7) has been used for isolating various target cells from whole blood (Table 1). The principle for specific cell capture is the combination of specific antibodies, well controlled shear stress conditions inside the device, and efficient passivation of the surfaces to prevent nonspecific binding of unwanted cells. Following optimization, the purity of cell capture can be as high as 99% and the yield of capture as high as 80%. One approach for increasing the purity in unfavorable situations relies on the use of isolation chambers in series (FIG. 8), where the first chamber depletes the cells that would otherwise contaminate the sample of interest in the second chamber. The captured cells can be imaged using standard microscope (FIG. 9), counted, and RNA and protein extracted (FIG. 10) for further analysis.

Example 3

HIV-Specific CD8 T Cell Isolation

Figure 11:
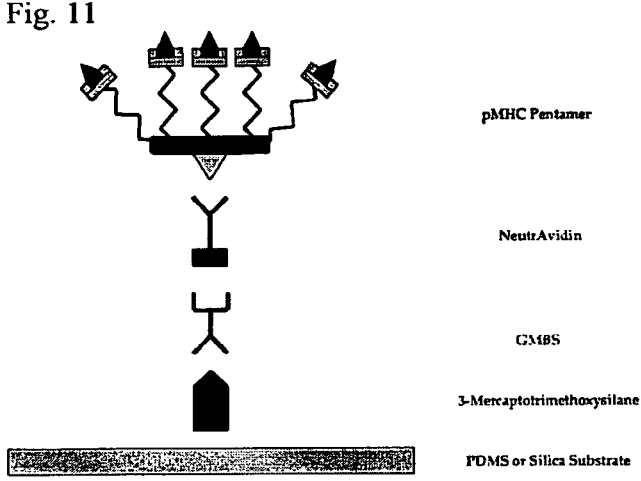
FIG. 11 is a schematic illustrating coupling of the pMHC pentamer molecules to a microfluidic channel.
Figure 12:
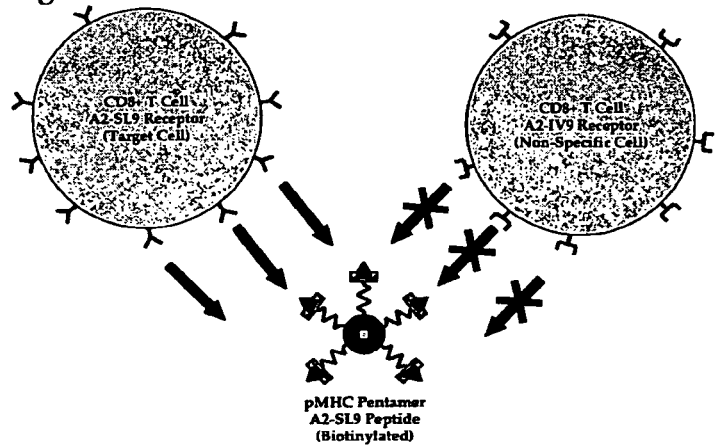
FIG. 12 is a schematic illustrating pMHC pentamers loaded with A2-SL9 antigenic peptide are specifically recognized by CD8+ T cells with receptors for this antigen, while non-specific CD8+ T cells (and all other cell populations) will not bind to the biotinylated pentamer.

We developed a PDMS microfluidic device coated with pMHC class I pentamers for the capture of disease-specific CD8+ T cells (FIG. 11). In our experiments, we used soft lithography and SU-8 fabrication techniques to create microchannels within a PDMS mold. The PDMS mold and a silica substrate were then exposed to oxygen plasma treatment before being irreversibly sealed together. The hydroxyl groups on the PDMS and silica surfaces were then treated with 3-mercaptotrimethoxysilane in anhydrous ethanol, resulting in the formation of thiol-terminal groups. After washing off unreacted silane solution with anhydrous ethanol, the PDMS device was flushed with the heterobifunctional crosslinker GMBS in anhydrous ethanol, during which the thiol group on the silane reacts specifically and covalently with the maleimide region of GMBS. This leaves the succinimide residue of the GMBS available for protein attachment, and after flushing unreacted GMBS with 1×PBS (pH 7.4), NeutrAvidin solution (in PBS) was introduced into the channel, resulting in the binding of the GMBS succinimide group to the terminal amino group of NeutrAvidin. After flushing unreacted NeutrAvidin with 1×PBS (pH 7.4), biotinylated pMHC class I pentamers loaded with A2-SL9 antigenic peptide (a dominant HIV gag epitope) were introduced into the device. The device was then flushed with 1×PBS (pH 7.4) with 1% BSA (w/v) for the purpose of flushing out unreacted pMHC pentamer and for minimizing non-specific cell interactions with the channel surface (FIG. 12).

With the device properly equipped for cell capture experiments, we cultured two clonal CD8+ T cell lines—one specific for the HIV A2-SL9 (SLYNTVATL) peptide, and one specific for an unrelated A2-IV9 (ILKEPVHGV) peptide. T cells that recognize these peptides in the context of the MHC class I molecule are present in most individuals infected with HIV.

Figure 13:
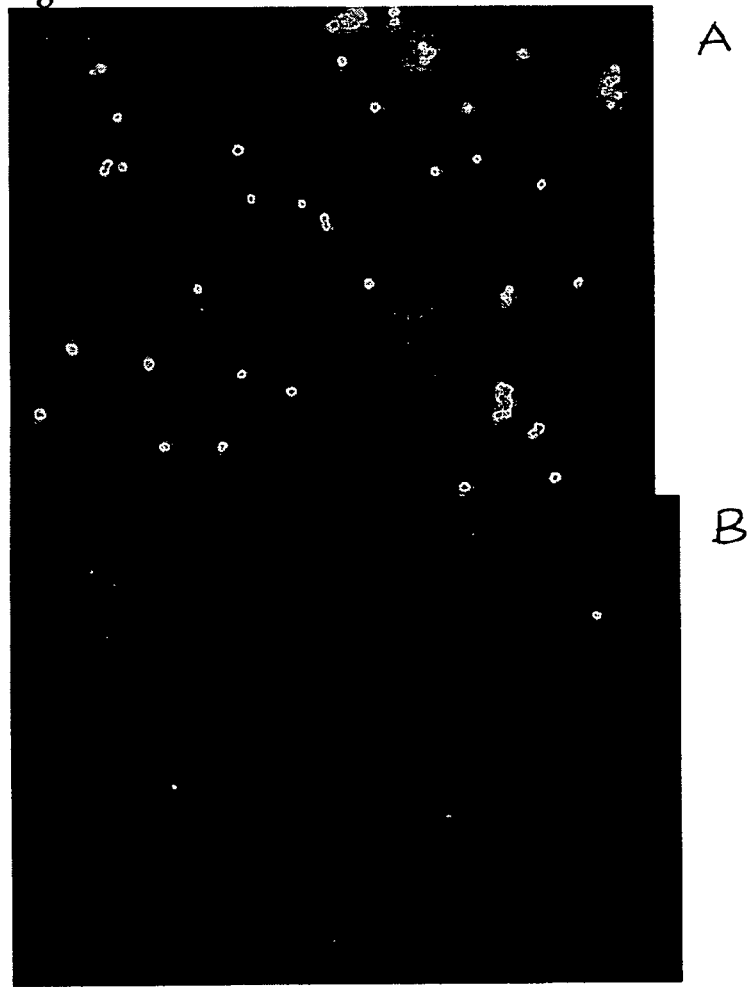
FIGS. 13A and 13B are photomicrographs showing capture of pure clonal populations of (A) A2-SL9 CD8+ T cells and (B) A2-IV9 CD8+ T cells using a PDMS microfluidic device coated with pMHC pentamers loaded with A2-SL9 antigenic peptide.

We introduced 500,000 A2-SL9 CD8+ T cells (125 microliters at a concentration of 4×10$^6$ cells/ml) into a PDMS microfluidic device functionalized with A2-SL9-loaded pMHC pentamers, at a flow rate of 2 μl/min. As a negative control, T cells specific for recognizing A2-IV9 were introduced into an identical device with the same specifications. The devices were flushed with 1×PBS to remove unattached cells from the channel surface, and then fixed with 1% PFA solution and fluorescently stained using DAPI solution before being imaged (FIG. 13). We observed a high degree of specific capture in the device with A2-SL9 CD8+ T cells, while a low level of non-specific T cell capture is seen in the device into which A2-IV9-specific CD8+ T cells were introduced. Specific T cell binding was efficient, as evidenced by a lack of a monolayer of cell coverage in the channel. This set of experiments established that disease-specific T cells can be isolated in microfluidic channels using pMHC complexes as capture agents. These devices have applications for disease diagnosis, or for studies where identification of disease-specific T cells are desirable, such as monitoring of vaccine efficacy.

Example 4

Capture of Tumor Cells Using Anti-EpCAM Antibodies

Figure 14:
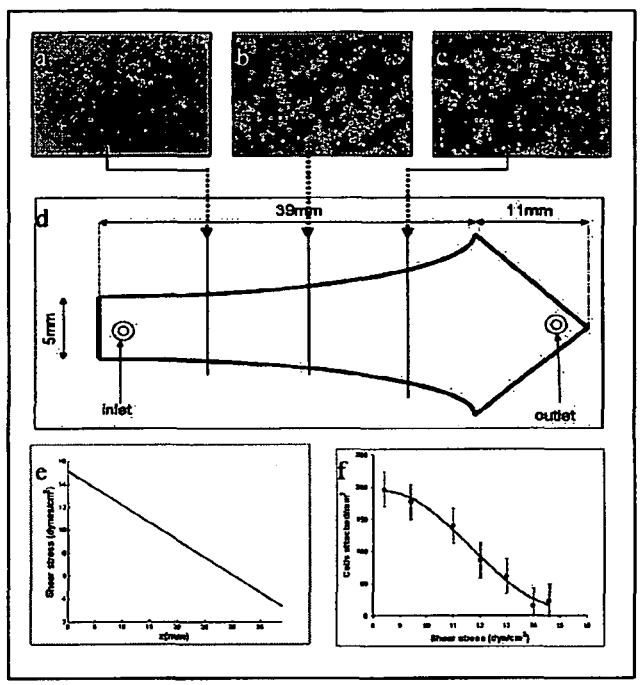
FIGS. 14A-14C are photomicrographs of captured cells in whole blood.
FIG. 14D is a schematic illustrating a channel from which the cells depicted in FIGS. 14 A-C were obtained.
FIG. 14E is a graph showing shear stress as a function of distance from the results of a concordance experiment to test experimental variability. Two experiments were run using the same sample under identical conditions.
FIG. 14F is a graph showing attached cells as a function of shear stress in a comparison of capture efficiency between whole blood and lysed RBC blood.

Shear stress plays an important role in cell capture. An optimum shear stress should be applied such that one can capture a maximum number of cancer cells at high enough flow rates. To find optimal flow rate, we studied the effect of shear stress on the cell capture using flat microfluidic chambers with variable width and constant height along the chamber. The geometry of these chambers shown in FIG. 14 is such that the shear stress varies linearly along the chamber length (FIG. 14E), permitting the study of a wide range of shear stresses for a given flow rate. Cultured lung cancer cells were spiked into PBS solution, and then passed through the Hele-Shaw chambers functionalized with EpCAM Ab at a constant flow rate. As the shear stress decreases along the channel, the density of the cells adhered to the surface increases (FIGS. 14A-14C). The effect of shear stress on the cell adhesion through EpCAM antibody-antigen binding is plotted in FIG. 14F show 8 dyn/cm$^2$ is the optimum shear rate, resulting in the capture of 200 cells/mm$^2$ of functionalized capture surface.

Other Embodiments

All publications, patents, and patent applications mentioned in the above specification are hereby incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

What is claimed is:

1. A method for isolating CD4+ lymphocytes from a sample of whole blood, the method comprising:
    (a) introducing said sample into a microfluidic device coated with binding moieties that bind to a cell surface marker of said CD4+ lymphocytes; and
    (b) applying a controlled shear stress from greater than 0.5 dyn/cm$^2$ to less than about 7.0 dyn/cm$^2$ to said sample in the microfluidic device, wherein the shear stress is low enough to allow binding of the binding moieties to said CD4+ lymphocytes expressing the cell surface marker at a first concentration and great enough to inhibit binding of the binding moieties to undesired CD4+ monocytes that express the same cell surface marker at a second concentration lower than the first concentration.

2. The method of claim 1, wherein said binding moieties are anti-CD4 binding moieties selected from the group consisting of antibodies, antibody fragments, oligopeptides, polypeptides, aptamers, oligonucleotides, coordination complexes, synthetic polymers, and carbohydrates.

3. The method of claim 2, wherein said sample is obtained from a patient at risk of developing AIDS.

4. The method of claim 1, further comprising (c) analyzing at least one biological property of said CD4+ lymphocytes.

5. The method of claim 4, wherein said biological property is selected from the group consisting of: mRNA expression, protein expression, DNA quantification, DNA sequence, and chromosomal abnormalities.

6. The method of claim 2, further comprising: (c) counting said CD4+ lymphocytes that bind to said binding moieties.

7. The method of claim 6, further comprising using said count to diagnose a disease state.

8. The method of claim 1, wherein binding of said CD4+ lymphocytes to said binding moieties occurs simultaneously with the application of the controlled shear stress.

9. The method of claim 1, wherein the controlled shear stress is between about 1 dyn/cm$^2$ and about 3 dyn/cm$^2$.

10. The method of claim 1, wherein the controlled shear stress is between about 0.7 dyn/cm$^2$ and about 5.0 dyn/cm$^2$.

11. The method of claim 1, wherein the controlled shear stress is between about 0.7 dyn/cm$^2$ and about 4.0 dyn/cm$^2$.

* * * * *